US006445491B2

(12) United States Patent
Sucha et al.

(10) Patent No.: US 6,445,491 B2
(45) Date of Patent: *Sep. 3, 2002

(54) METHOD AND APPARATUS FOR OPTICAL SECTIONING AND IMAGING USING TIME-GATED PARAMETRIC IMAGE AMPLIFICATION

(75) Inventors: Gregg Sucha, Manchester; Anand Hariharan; Donald J. Harter, both of Ann Arbor, all of MI (US); Jeff Squier, San Diego, CA (US)

(73) Assignee: Irma America, Inc., Ann Arbor, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/239,667

(22) Filed: Jan. 29, 1999

(51) Int. Cl.[7] ................................................. G06F 1/39

(52) U.S. Cl. ...................................... 359/330; 359/326

(58) Field of Search ................................. 359/326–330

(56) References Cited

U.S. PATENT DOCUMENTS

| 3,629,602 A | 12/1971 | Firester ....................... 359/330 |
| 5,585,913 A | 12/1996 | Hariharan et al. .......... 356/4.09 |
| 5,778,016 A | 7/1998 | Sucha et al. .................... 372/38 |
| 5,936,739 A * | 8/1999 | Cameron et al. ........ 359/330 X |

OTHER PUBLICATIONS

Optics Letters, vol. 11, No. 3, Mar. 1986 "Femtosecond Optical Ranging in Biological Systems", pp. 150–152, Fujimoto et al.

Optics Letters, vol. 17, No. 2, Jan. 15, 1992 "High–Speed Optical Coherence Domain Reflectometry", pp. 151–153, Swanson et al.

Revue Phys. Appl. 22 (1987) Dec., 1987 "Ultrafast Diagnostics", pp. 1605–1611, Diels et al.

Applied Optics, vol. 31, No. 32, Nov. 1992, "Imaging with Femtosecond Pulses", Chi Yan and Jean–Claude Diels, pp. 6869–6873.

(List continued on next page.)

Primary Examiner—John D. Lee
(74) Attorney, Agent, or Firm—Sughrue Mion, PLLC

(57) ABSTRACT

An optical parametric amplifier pumped by ultrashort optical pulses provides time-gated image amplification or time-gated image frequency conversion, resulting in optical sectioning of an object under test and/or background rejection of improperly timed light. An ultrashort laser pulse of one frequency is used to illuminate an object under test. An ultrashort pulse light beam at a signal frequency transmitted through or scattered from the object is optically mixed with an ultrashort laser pulse at a pump frequency in a nonlinear optical medium. This mixing produces an amplified image of a particular optical section of the object at the signal frequency in addition to producing a frequency converted image of the same optical section at an idler frequency. This time-gated amplification can be used in conjunction with a confocal imaging system, or a conventional imaging system. The resolution of optical sectioning is determined by the temporal widths of the signal and pump pulses and by the group velocity walkoff in the nonlinear medium. By illuminating the target with a train of closely spaced ultrashort pulses, an image of multiple sections can be amplified and downconverted within a single laser shot, giving a contour image of the target. The signal light can also be fluorescence from the object, excited by a short laser pulse, either through single-photon or multi-photon absorption. In this case, the signal light is incoherent with respect to the pump light. By using quasi-phase-matched nonlinear optical crystals as the amplifying medium, advantages such as an increased acceptance angle and lower pump thresholds are obtained.

76 Claims, 9 Drawing Sheets

OTHER PUBLICATIONS

J. Watson et al, "Imaging in Diffuse Media with Ultrafast Degenerate Optical Parametric Amplification", Optics Letters, vol. 20, p. 231 (Feb. 1995).

J.A. Valdmanis et al, "Three–dimensional Imaging with Femtosecond Optical Pulses", Optical Society of America, conference on Lasers and Electro–Optics, vol. 7, paper CTUA1, May 22, 1990.

M.A. Duguay et al, "Ultrahigh Speed Photography of Picosecond light pulses and Echoes", Appl. Opt., vol. 10, No. 9, pp. 2162–2170, Sep. 1971.

L. Wang et al, Science, vol. 253, p. 769, Aug. 1991, Ballistic 2–D Imagining Through Scattering Walls Using an Ultrafast Optical Kerr Gate.

K.M. Yoo et al, Optics Letters, vol. 16, No. 13, p. 1019 "Imaging objects hidden in highly scattering media using femtosecond–harmonic–generation cross–correlation time gating" Jul. 1, 1991.

M. Yamada et al. in Appl. Phys. Lett., vol. 62, p. 436, Feb. 1993, "First–order quasi–phase matched $LiNbO_3$ waveguide periodically poled by applying an external field for efficient blue second–harmonic generation".

M.I. Kolobov et al. "Sub–shot–noise microscopy: imaging of faint phase objects with squeezed light," Optics Letters, vol. 18, p. 849, Jun. 1, 1993.

M. Gu et al. "Three–dimensional image formation in confocal microscopy under ultra–short–laser–pulse illumination," Journal of Modern Optics, vol. 42, No. 4, pp. 747–762 (1995).

M. Gu et al., "Effects of a finite–sized pinhole on 3D image formation in confocal two–photon fluorescence microscopy," Journal of Modern Optics, vol. 40, No. 10, pp. 2009–2024 (1993).

S. Hell et al., "Pulsed and cw confocal microscopy; a comparison of resolution and contrast," Optics Communications, vol. 113, pp. 144–152, Dec. 15, 1994.

M. Müller et al. in "3D–microscopy of transparent objects using third–harmonic generation," Journal of Microscopy, vol. 191, No. 3, pp. 266–274, Sep. 1998.

Izatt et al. in "Optical coherence microscopy in scattering media," Optics Letters, vol. 19, p. 590, Apr. 15, 1994.

R. Trebino et al., "Measuring ultrashort laser pulses in the time–frequency domain using frequency–resolved optical gating," Rev. Sci. Instrum. 68 (9), Sep. 1997, p. 3277.

A. Buist et al. "Double–pulse fluorescent lifetime measurements," Journal of Microscopy, 186 (3) 212, Jun. 1997.

* cited by examiner

METHOD AND APPARATUS FOR OPTICAL SECTIONING AND IMAGING USING TIME-GATED PARAMETRIC IMAGE AMPLIFICATION

BACKGROUND OF THE INVENTION

1. Field of the Invention

The present invention relates to laser-based imaging systems which are used for time-gated imaging, imaging through turbid media, optical sectioning, metrology, image amplification, frequency conversion of images, and confocal microscopy.

2. Description of the Related Art

Research relating to optical parametric image amplification has concerned the upconversion of weak infrared images, and the selective amplification of certain spatial frequencies without regard to time resolution. As reported by J. Watson et al. in "Imaging in diffuse media with ultrafast degenerate optical parametric amplification," Optics Letters, Vol. 20, p. 231 (1995), time-resolved, degenerate optical parametric image amplification has been used for transillumination imaging through turbid media by providing a sub-picosecond time gate to temporally discriminate against scattered photons. This method, however, does not provide optical sectioning of the object or surface contour information. These optical parametric amplification (OPA) imaging techniques have employed the OPA either at an image plane or in the Fourier plane of the optical system.

Ultrafast time-gated imaging has also been employed to observe fast processes, such as the propagation of light pulses through various media. Time-gating has been performed using techniques other than optical parametric amplification. These techniques include: LIF holography, as disclosed by J. A. Valdmanis et al. in "Three-dimensional imaging with femtosecond optical pulses," Optical Society of America, Conference on Lasers and Electro-Optics, Vol. 7, paper CTUA1, (1991); picosecond Kerr shutters, as disclosed by M. A. Duguay et al. in "Ultrahigh speed photography of picosecond light pulses and echoes," Appl. Opt., Vol. 10, pp. 2162–2170 (1970) and by L. Wang, et al. in Science, Vol. 253, p. 769 (1971); and sum-frequency cross-correlation, as disclosed by K. M. Yoo et al. in Optics Letters, Vol. 16, p. 1019 (1991). Time-gated upconversion using pulses as short as 65 fsec has been used to measure biological specimens such as the corneal structure of rabbit eyes, as disclosed by Fujimoto et al. in "Femtosecond optical ranging in biological systems," Optics Letters, Vol. 11, p. 150 (1986). In this method, the ranging was performed one point at a time, and required raster scanning of the beam over the specimen.

Subsequently, an optical coherence tomography (OCT) technique was disclosed by E. A. Swanson et al. in "High-speed optical coherence domain reflectometry," Optics Letters, Vol. 17, p. 151 (1992), which employs only linear interferometry without any nonlinear optical interaction. Time-gated imaging by ultrashort pulses using second harmonic generation (SHG) was first disclosed by Diels et al. in "Imaging with femtosecond pulses," Appl. Opt., Vol. 31, p. 6869 (1992) and in "Ultrafast diagnostics," Revue Phys. Appl., Vol. 22, p. 1605 (1987). In this method, a gating pulse was used to time-gate and upconvert entire images of objects which were illuminated by an ultrashort pulse. However, this method does not provide any amplification of the image, and provides only a single contour or surface section.

Surface metrology measurement using ultrafast lasers in conjunction with sum-frequency mixing is disclosed in U.S. Pat. No. 5,585,913 to Hariharan, et. al., entitled "Ultrashort pulsewidth laser ranging system employing a time gate producing an autocorrelation and method therefor." In this method, a focused laser beam is scanned over the surface of the target in order to map out the surface topography. Again, in this method, there is no light amplification, and raster scanning is required to build up an image of a surface.

SUMMARY OF THE INVENTION

It is an object of the present invention to employ optical parametric amplification (OPA) in conjunction with conventional, Fourier or confocal imaging systems to achieve high gain and low noise amplification of signal light reflected from or transmitted through an object in order to produce an amplified image of the object.

It is a further object of the present invention to improve image resolution in confocal microscopy using optical parametric amplification.

It is another object of the present invention to use the time gating capability of optical parametric amplification to discriminate against scattered light.

A further object of the present invention is to use the time-gating capability of optical parametric amplification to provide optical sectioning of an object under test, similar to that obtained with optical coherence tomography (OCT).

A still further object of the present invention is to use the time gating capability of optical parametric amplification to produce a new method of fluorescence lifetime imaging.

Another object of the present invention is to use quasi-phase-matched nonlinear optic materials as the amplifying medium in an imaging system, thereby providing large angular acceptance and low pump thresholds.

Yet another object of the present invention is to lower the required excitation power of an illuminating beam in an imaging system, thereby allowing increased observation time, reducing photobleaching and enhancing the viability of cells being imaged.

The aforesaid objects are achieved individually and in combination, and it is not intended that the present invention be construed as requiring two or more of the objects to be combined unless expressly required by the claims attached hereto.

The present invention employs optical parametric amplification (OPA) in a nonlinear optical medium pumped by an ultrashort (less than 2 ns) pulse laser at frequency $\omega_p$, to amplify and time-gate the scattered light from a target object illuminated by an ultrashort laser pulse at a signal frequency $\omega_s$. In the process, another amplified signal is generated at the idler frequency, $\omega_i$. This amplified light is recorded using a CCD camera or other imaging device. This technique can be used in conjunction with confocal imaging methods. By amplifying and time-gating the scattered light, optical sectioning of the object is achieved, enabling an image of an isometric contour of the object surface or interior to be produced. In the case of nondegenerate OPA, detection of the idler frequency instead of the signal frequency also achieves frequency conversion of the image. Standard gated image intensifiers (e.g., microchannel plates) have a time-gate window of approximately 100 ps which can resolve depth features with only approximately 1 cm resolution. By using ultrashort pulses (e.g., 100 fs) it is possible to resolve surface features with a resolution of approximately 10 microns. By using still shorter pulses, the longitudinal resolution improves further (e.g., down to 2 microns using 20 fs pulses).

Sum-frequency gating and Kerr gating yield comparable resolution when pumping with ultrashort pulses, but do not provide amplification, and, in fact, usually are most inefficient. Photon efficiencies typically do not exceed 10% with these systems. In contrast, by using ultrafast, time-gated, optical parametric image amplification (UTOPIA) it is possible to obtain both image amplification and time-gating simultaneously. The parametric amplification method of the present invention can be performed in collinear or noncollinear geometries, can be either degenerate or nondegenerate, and can employ type-I or type-II phase matching or quasi-phase matching.

Further, the technique of the present invention can be used in conjunction with either a confocal imaging system or a conventional or Fourier imaging system. If collinear, degenerate OPA is used, then the amplified contour image is superimposed on the unamplified image at the same frequency (since the idler frequency $\omega_i$ is the same as the signal frequency $\omega_s$). This provides a convenient method of registration between the contour image and the visual image of the object. With degenerate OPA, the image amplification factor is sensitive to the relative optical phase between the pump and signal pulses. In some cases it may be desirable to obtain only the contour image with maximum discrimination against any background light. In these cases, it is advantageous to use nondegenerate UTOPIA which gives simultaneous image amplification, time-gating, and frequency conversion to the idler frequency. Illumination of the target with pulses at a wavelength near 1550 nm is particularly advantageous in many cases because this wavelength is considered to be eyesafe.

By illuminating the target with a single pulse, an isometric contour (or contours) corresponding to a particular depth level of the target surface (i.e., an optical section) is obtained. Then, by adjusting the optical path length (time delay) traversed by either the pump or signal pulses, a number of different contours can be obtained, whose spacings correspond to the adjustments in optical path difference. Thus, a multiple contour image can be built up from a number of single-contour images. If, instead, the target is illuminated by a sequence of N closely-spaced ultrashort pulses during the pump pulse period, then a multiple contour image with the contours corresponding to N different depth levels of the target surface is obtained with a single pump pulse. If the pump laser pulse is sufficiently powerful, then this multiple-contour image can be acquired using a single laser shot, making it possible to obtain topographic images of objects which are moving very rapidly, e.g., even at hypersonic velocities. While multiple-contour images have been obtained using interferometric methods, the contours so obtained are very closely spaced (e.g., at a fixed spacing of one wavelength of the light) which gives very high resolution, and which limits the total depth which can be probed with a CCD imaging system due to the finite number of pixels which comprise the CCD array. The UTOPIA system of the present invention can cover a large dynamic range in feature depth by adjusting the spacings between the optical pulses in the sequence. With resolution of 10 microns, it is still possible to map out a depth range of over 100 mm with no ambiguity.

The choice of the nonlinear optical medium for performing optical parametric amplification is an important aspect of the present invention. The advantages of using a noncritical phase matching geometry have been demonstrated in type I nonlinear crystals. Quasi-phase-matched crystals have significant advantages over type I and type II phase-matched crystals, as described by M. Yamada et al. in Appl. Phys. Lett., Vol. 62, p. 436 (1993). In particular, periodically--poled lithium niobate (PPLN) has a large nonlinear coefficient and can be tailored to the desired phase matching conditions, such as frequency and acceptance angle. PPLN enables noncritical phase matching, thus increasing the acceptance angle of the UTOPIA system. Thus, according to the invention, the nonlinear optical medium is preferrably a periodically poled ferroelectric optical material, including but not necessarily limited to lithium niobate, lithium tantalate, $MgO:LiNbO_3$, KTP and crystals of the KTP isomorph family.

The above and still further objects, features and advantages of the present invention will become apparent upon consideration of the following detailed description of specific embodiments thereof, particularly when taken in conjunction with the accompanying drawings wherein like reference numerals in the various figures are utilized to designate like components.

DESCRIPTION OF THE PREFERRED EMBODIMENTS

According to the present invention, ultrafast time-gated optical parametric image amplification (UTOPIA) is employed in conjunction with a variety of imaging systems such as conventional, Fourier, and confocal imaging systems. Advantageously, the present invention amplifies signal light via optical parametric amplification (OPA) which provides both high gain and low noise, e.g., gains of up to 80 dB are commonly obtained with OPA. Consequently, the quantum efficiency achieved by the present invention in the described imaging systems is much greater than with other techniques. As reported by M. I. Kolobov et al. in "Sub-shot-noise microscopy: imaging of faint phase objects with squeezed light," Optics Letters, Vol. 18, p. 849 (1993), parametric amplification in combination with imaging also holds the possibility of enabling sub-shot-noise imaging. In contrast to previous OPA imaging systems using ultrashort pulses, the UTOPIA system of the present invention can be used in reflection (in addition to transillumination), thus giving optical sectioning with depth resolution determined primarily by the pulsewidth. Also, the use of quasi-phase-matched (QPM) nonlinear media provides both high gain, noncritical phase matching, and large angular acceptance, thus increasing the field of view. Quasi phase matching has additional advantages over type-I and type-II phase matching in terms of background-free amplification and superior time (range) resolution. Nonlinear optical media which are preferred according to the invention include periodically poled ferroelectric optical materials, including lithium niobate, lithium tantalate, MgO:LiNbO$_3$, KTP and crystals of the KTP isomorph family.

Figure 1:
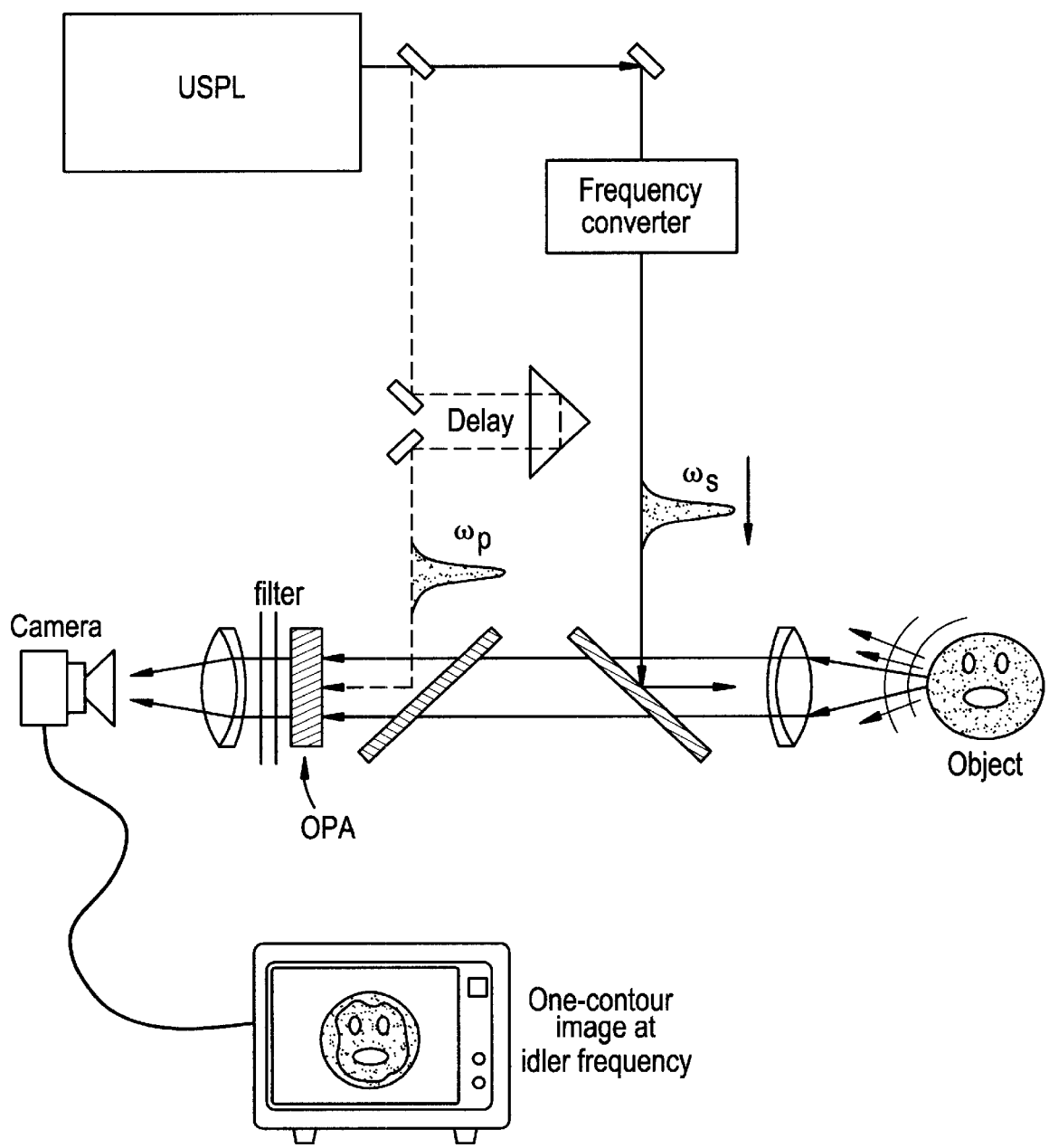
FIG. 1 is a schematic diagram of an optical parametric imaging system according to an exemplary embodiment of the present invention.

An ultrafast tomographic optical parametric image amplification system 10 for generating an image of a three-dimensional object under test according to an exemplary embodiment of the present invention is shown in FIG. 1. Imaging system 10 includes an ultrashort pulse laser (USPL) 12 which generates an ultrashort laser pulse at a pump frequency $\omega_p$. The ultrashort laser pulse from laser 12 is split into two beams, a pump beam and an illumination beam, by a beam splitter 14 or other conventional beam-splitting or beam-separating mechanism. The ultrashort pulse of the illumination beam is directed to a frequency conversion device 16, such as an optical parametric generator, which frequency converts the pulse to a signal frequency $\omega_s$ that is lower than the pump frequency $\omega_p$. The frequency-converted pulse at the lower, signal frequency $\omega_s$ is used as the signal pulse to illuminate a target object.

Imaging system 10 includes an image acquisition device 20, such as a charge-coupled device (CCD) camera, a focal plane array, or a vidicon used to form an image of the target object. For convenience, the image acquisition device 20 will hereinafter be referred to as a "camera" or "detector"; however, it will be understood that the image acquisition device can be any appropriate device for detecting or registering object image signals, including the aforementioned devices. The imaging system may have only one real image plane at the camera focal plane, or it may have one or more intermediate real image planes between the object and the camera. An imaging device 18 receives image signals acquired by camera 20 and generates an image from the image signals and/or records the image signals for later image generation. The imaging device 18 can comprise any conventional image generation and/or image storage device, including, but not limited to: a visual display (e.g., a cathode ray tube or a light emitting diode array), a printer, a photographic image generating device, and an image signal recording or storage device (e.g., video tape, RAM, etc.). It will be appreciated that, in addition to the imaging applications descried above and hereafter, the invention, wihtout necessarily imaging an object, finds application as a LIDAR system.

As shown in FIG. 1, the target object can be illuminated collinearly with the optical axis of the imaging system by projecting the signal pulse toward the object along the optical axis of the camera 20. Specifically, a beam splitter 21 lying along the optical axis of camera 20 directs the signal pulse through a lens system 23 toward the object. A nonlinear optical medium 22, such as periodically-poled lithium niobate (PPLN), is positioned at some arbitrary intermediate image plane in the imaging system along the optical axis of camera 20, and serves as an optical parametric amplifier. The signal pulse light scattered from the target is collected by lens system 23, passes through beamsplitter 21 and a dichroic mirror 25, and is imaged onto the nonlinear optical medium 22.

The pulse of the pump beam at the higher, pump frequency, $\omega_p$, is used as the pump pulse for the nonlinear optical medium 22. In order to controllably synchronize the arrival of the pump pulse and the reflected light of the signal pulse at the nonlinear optical medium 22, the pump pulse is time delayed by an adjustable or variable optical delay line 24. The pump pulse is then directed onto the nonlinear optical medium 22 by dichroic mirror 25. The pump pulse interacts with the signal radiation in the nonlinear optical medium 22 in such a manner that the nonlinear optical medium 22 amplifies portions of the image which arrive synchronously with the pump pulse at the nonlinear optical medium 22. Simultaneously, a frequency-converted image is generated at the idler frequency, $\omega_i$, which is different from the signal frequency $\omega_s$ in the case of nondegenerate optical parametric amplification (OPA).

A frequency-selective filter 26 is used to block the light at the pump and signal frequencies, allowing only the image at the idler frequency $\omega_i$ to pass through lens system 27 to the camera 20. The resulting image is a single contour or set of contours which all correspond to surface features which are equidistant (in terms of optical path length) from the reference plane, which can be defined as the input surface of the nonlinear optical medium 22. This contour is an amplified image of an optical section of the object under test. Because the detection is performed at the idler frequency, the detection is background free.

By changing the optical delay experienced by the pump pulse (i.e., by adjusting the adjustable optical delay line 24), a similar contour is obtained which corresponds to a different optical section of the object, displaced in depth from the previous section by an amount equal to the change in optical path length of the pump pulse. By repeatedly changing the optical delay of the pump pulse and acquiring contour images, a complete three-dimensional topographic image of the object surface or tomographic image of the object interior can be built up from a series of contour images.

The depth resolution is determined by the pulsewidths of the pump and signal pulses, and by the group velocity walkoff between the pump and signal pulses in the nonlinear optical medium 22. In the case where the illumination is not collinear, the image contours recorded by camera 20 do not correspond to sections which are equidistant from the optical axis, but which are skewed with respect to the optical axis; accordingly the detected image signals must be mathematically interpreted to account for the relative propagation angle.

While a blocking filter that passes the idler frequency and blocks the signal and pump frequencies advantageously eliminates background noise, the blocking filter can be configured to block the pump radiation at frequency $\omega_p$ and the idler radiation at frequency $\omega_i$ while passing the signal radiation at frequency $\omega_s$. In this arrangement, the image captured by the camera will consist of the amplified contour image (corresponding to the timing of the pump pulse)

superimposed on the unamplified image of the whole object surface which is not time gated. This combination of the amplified image section and the unamplified surface image provides a convenient means of registration between the visual image and the optical sections of the surface.

In the degenerate case, where the signal and idler frequencies are equal, the blocking filter blocks only the pump radiation at frequency $\omega_p$ and passes the amplified image at frequency $\omega_s=\omega_i$. In this case, the gain of the OPA is dependent on the relative optical phase between the pump and signal pulses when they are incident on the nonlinear optical medium 22.

Figure 2:
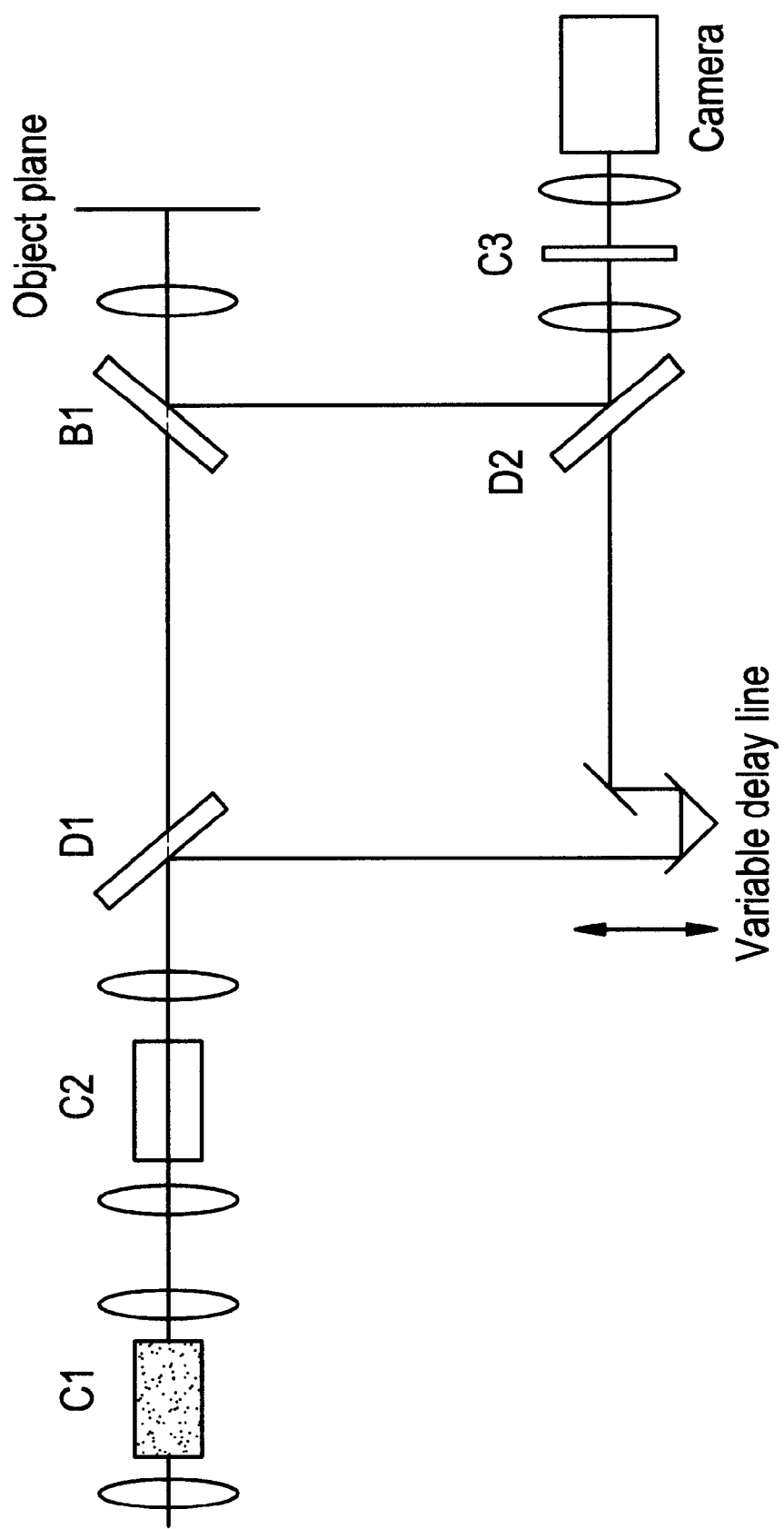
FIG. 2 is a schematic diagram of an apparatus used to experimentally demonstrate the fundamental operation of an imaging system employing parametric image amplification with ultrashort pulses.

Referring to FIG. 2, a schematic diagram of an apparatus 30 used to experimentally demonstrate the operational principles of parametric image amplification with ultrashort pulses is shown. Pulses from a fiber chirped pulse amplification (CPA) system are produced at a wavelength of 1550 nm, giving 70 mW average power, at a repetition frequency of 20 kHz, and a pulse energy of 3.5 $\mu$J. These pulses are incident at the input of the apparatus 30, where they are frequency doubled by a frequency-doubling crystal 32 to produce 30 mW of 780 nm light. This light powers an optical parametric generation (OPG) crystal 34, which is tuned to produce 1300 nm wavelength radiation. The residual 780 nm pump light is separated from the 1300 nm light through a dichroic 36. The pulses widths are approximately 700 fs in duration. The 1300 nm light is used to illuminate the object, while the 780 nm light is used to pump a periodically poled lithium niobate (PPLN) crystal 38, which is the nonlinear optical material used to provide the image amplification. More specifically, a beam splitter 40 directs the reflected illumination light toward a dichroic 42 which combines the reflected illumination light with the pump pulse and directs them toward the PPLN crystal 38. The 1300 nm light reflected from the object is passed through the PPLN crystal 38 so as to be co-propagating with the pump beam. The delay between the 1300 nm light reflected from the object and the 780 nm pump light is adjusted by a variable delay line 44 to provide optimal temporal overlap (and thus optimal gain) in the PPLN crystal. The output of the PPLN crystal is then imaged onto a camera 46, and the image is detected at 1300 nm (in this experimental configuration, a frequency filter is placed between the PPLN crystal 38 and the camera 46).

Using the experimental configuration shown in FIG. 2, the amplification was first tested simply by using a mirror as an object, resulting in the amplification of the 1300 nm pulse by a factor of 300–350 when a pump pulse of 71 nJ at 780 nm was used. The approximate beam area over which amplification occurred was 76 $\mu$m.

The time gating aspect of the present invention was illustrated by tuning the OPG crystal 34 to create many satellite pulses, up to sixteen, separated in time. With the pump arm blocked (i.e., the pump pulse was prevented from reaching the PPLN crystal 38), only a low background was detected by the camera 46. With the pump arm unblocked, an image of the illumination beam appeared. This image could be made to appear and disappear depending on the timing of the pump beam pulse, indicating that selective amplification of the individual satellite pulses was taking place. This amplification was verified independently by cross correlating the output.

Figure 3:
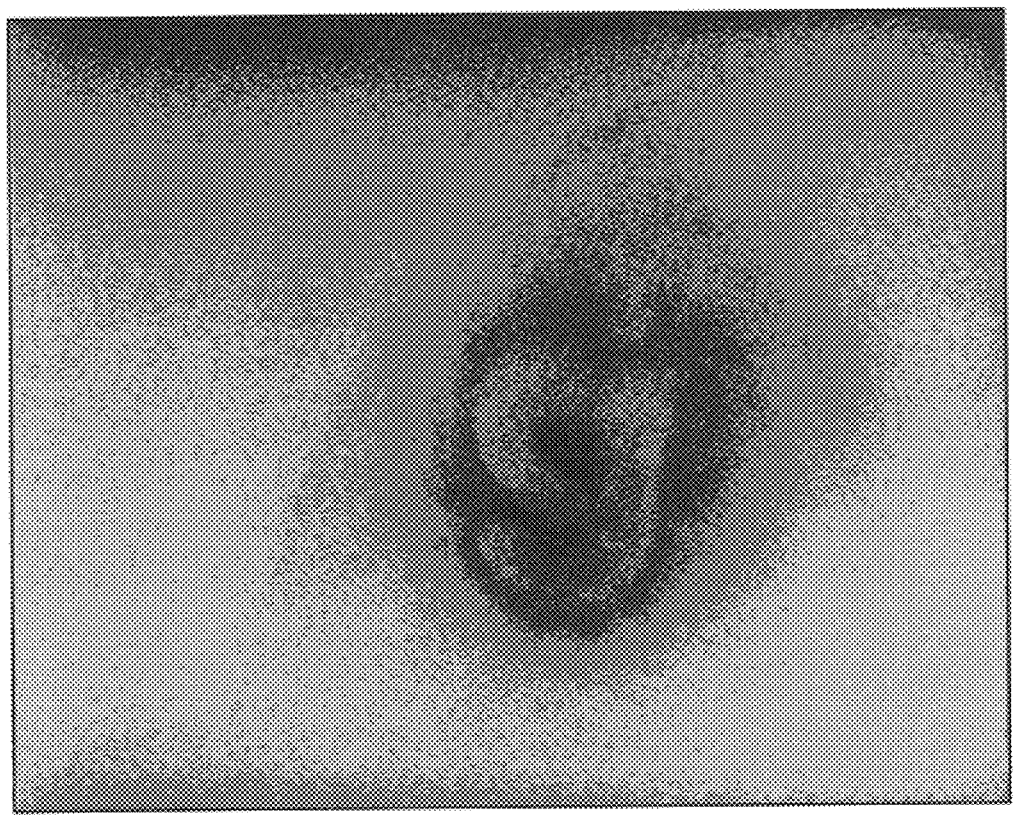
FIG. 3 is a weakly amplified, magnified image of the letter "a" created by a mask in the object plane of the imaging system illustrated in FIG. 2.

Next, a small, thin mask of the letter "a" was placed at the object plane. The "a" itself was black and of low reflectivity. The mask was placed directly on the mirror, consequently producing a reverse contrast image. The "a" is formed at the camera by the absence of light, i.e., the image appears where there is no light. The 1300 nm illumination beam was just large enough to slightly overfill the mask. The image resulting from weakly amplified 1300 nm pulses is shown in FIG. 3. Note that the image contrast is degraded due to light spilling over into areas of the "a" but nonetheless it is visible and distinguishable. This degraded image is attributable to spatially nonuniform gain due to the beam profile of the pump beam; i.e., the highest gain is at the center of the beam.

When the timing delay between the reflected and pump pulses is changed by more than a pulsewidth, the image disappears, demonstrating the time-gating aspect of the system. It should also be noted that the image is magnified by approximately a factor of five, so the system forms a low-power, wide-field microscope.

Figure 4:
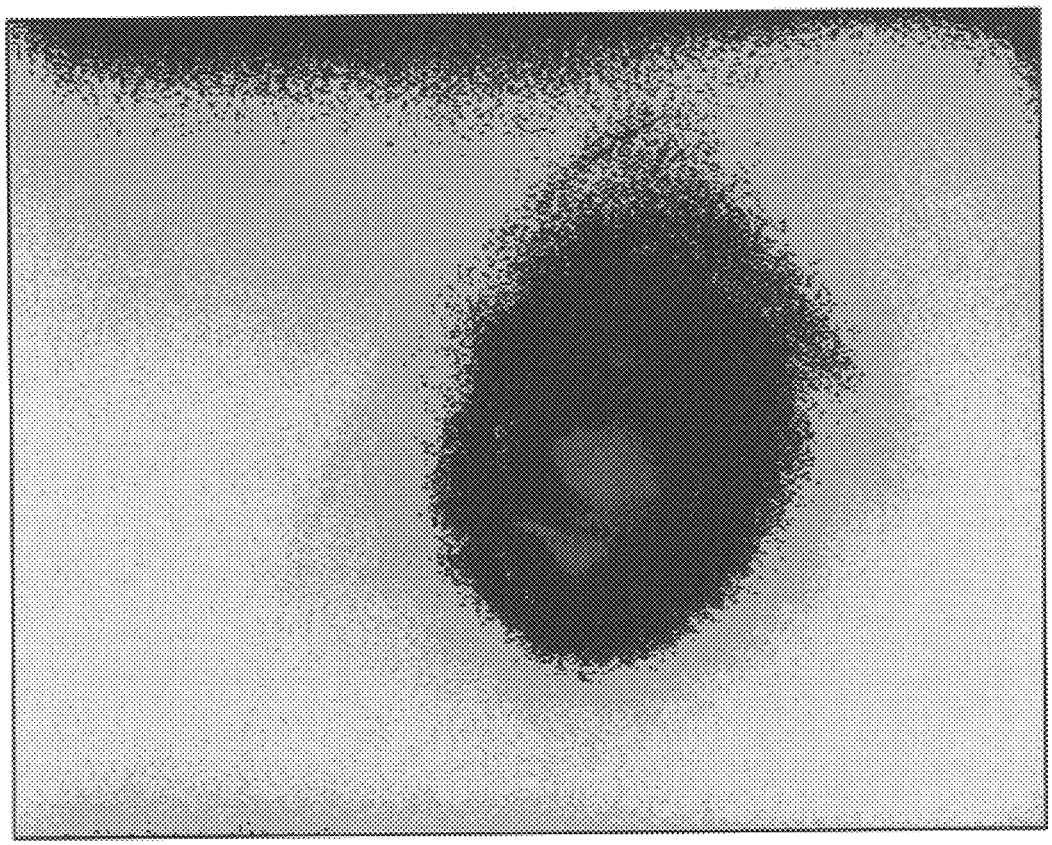
FIG. 4 is a strongly amplified, magnified image of the letter "a" using the imaging system illustrated in FIG. 2.

In FIG. 4, a strongly amplified image is shown. The image areas of greatest intensity show the highest gains. That there is more gain at the center of the image than at the edges is due to the fact that a Gaussian beam mode is used in both the illumination and pump beams. Thus, the field is not flat in amplitude. Contrast in the image is reduced, but this is believed to be due to a combination of the low initial image contrast, and lack of dynamic range of the camera. The stronger amplification in the case of FIG. 4 is obtained by timing the reflected and pump pulses so that they are more closely coincident within the nonlinear optical medium.

Thus, the parametric amplification of a magnified image has been demonstrated using the experimental apparatus shown in FIG. 2. The measured gains, and pump fluences demonstrate that this technique can be readily scaled to a confocal microscope system using presently available lasers, microscopes, nonlinear media, and detectors.

Figure 5A:
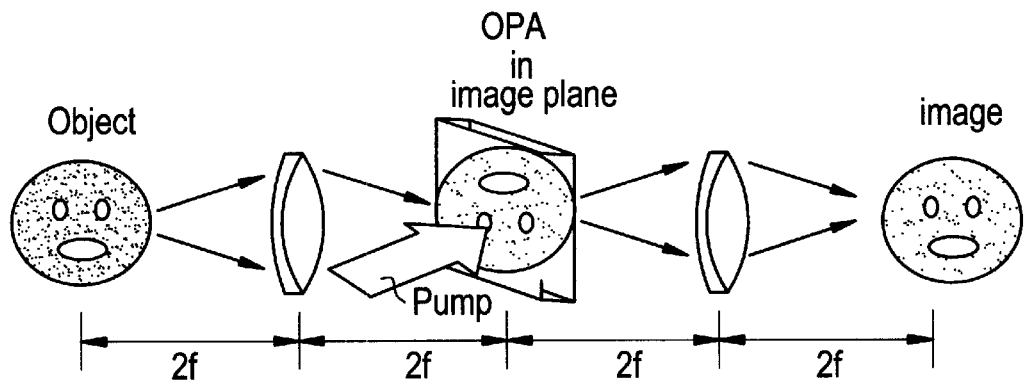
FIGS. 5(a)–5(c) are schematic diagram illustrating that the nonlinear optical medium of the imaging system of the present invention can be positioned in an image plane, the Fourier plane, or some other arbitrary plane of the imaging system.
Figure 5B:
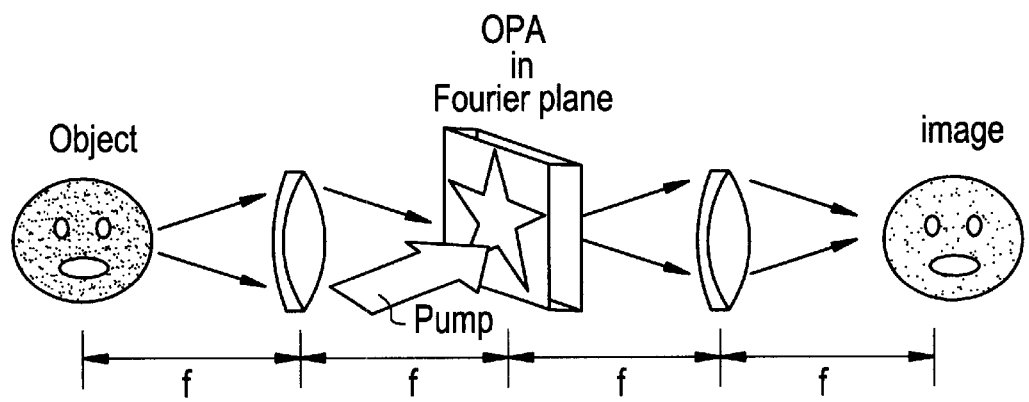
Figure 5C:
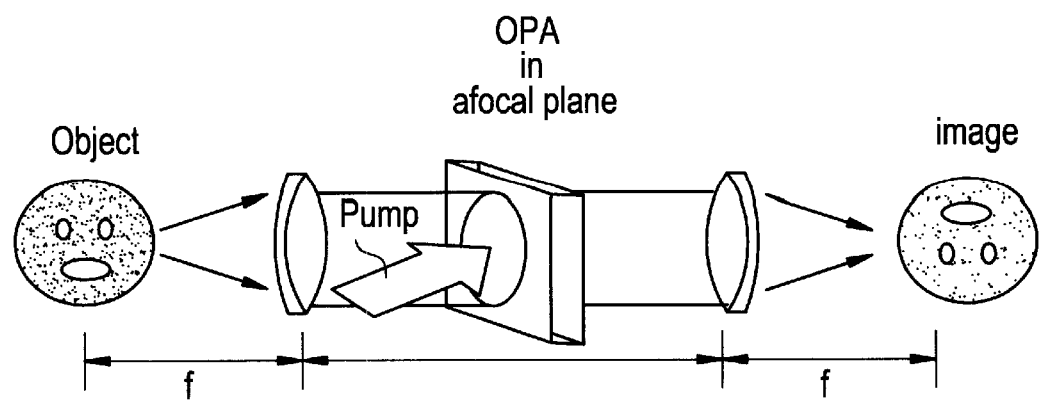

As shown in FIG. 5($a$), the nonlinear optical medium can be positioned at or near a real image plane of the object in the imaging system. As shown in FIG. 5($b$), the nonlinear optical medium can also be positioned at or near a Fourier plane of the object in the imaging system, resulting in a reduction in the degradation of resolution of the target radiation which normally accompanies optical parametric nonlinear interactions in a medium of finite thickness, as pointed out in U.S. Pat. No. 3,629,602, to Firester. The amplified radiation at either $\omega_s$ or $\omega_1$ must then, in turn, be optically Fourier transformed back to a real image of the object. This can be accomplished by a single lens in the simplest case. The imaging system may not have any real image plane within the system between the object and the camera. In this case, the nonlinear optical medium is inserted at any arbitrary plane between the object and the camera, as shown in FIG. 5($c$).

Figure 6:
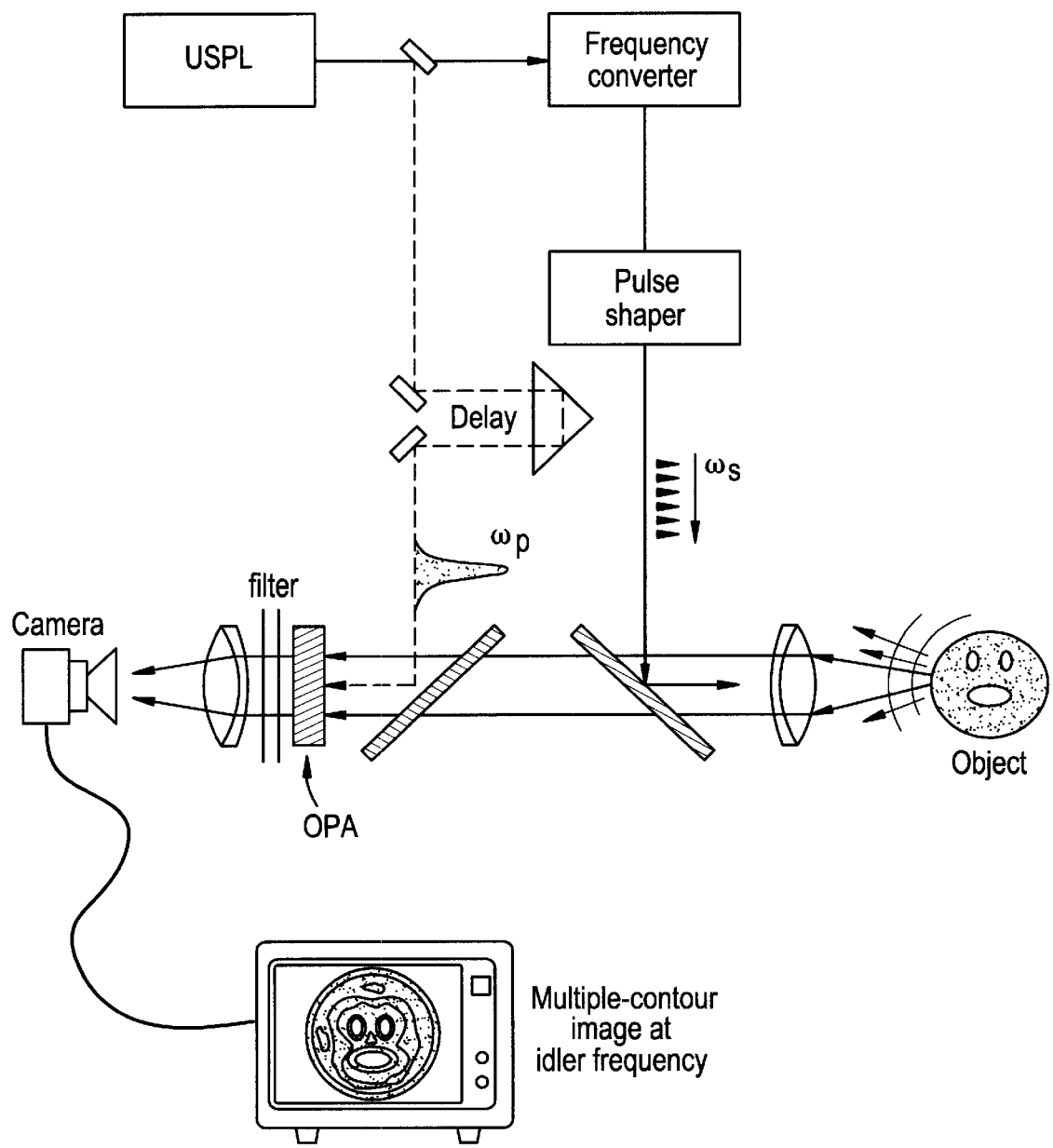
FIG. 6 is a schematic diagram of an imaging system according to another embodiment of the present invention in which the target is illuminated by a sequence of pulses to produce a multiple-contour image from a single laser shot.

FIG. 6 is a schematic diagram illustrating an imaging system 60 according to another embodiment of the present invention in which the target is illuminated by a sequence of N pulses at the signal frequency $\omega_s$. The pulse sequence is obtained by passing the signal pulse through a pulse shaper 62. The scattered target radiation is then selectively, parametrically amplified in the nonlinear optical medium by interaction with the pump pulse. Only those portions of the radiation are amplified which correspond to particular sections of surface, resulting in a multiple contour image of the object surface. The longitudinal separation between sections of surface corresponds to the spacing between signal pulses emanating from the pulse shaper 62 and illuminating the target. It is thus possible to obtain a multiple contour image of the target surface using a single laser shot without recourse to adjusting the optical path length traversed by the pump pulse.

Figure 7:
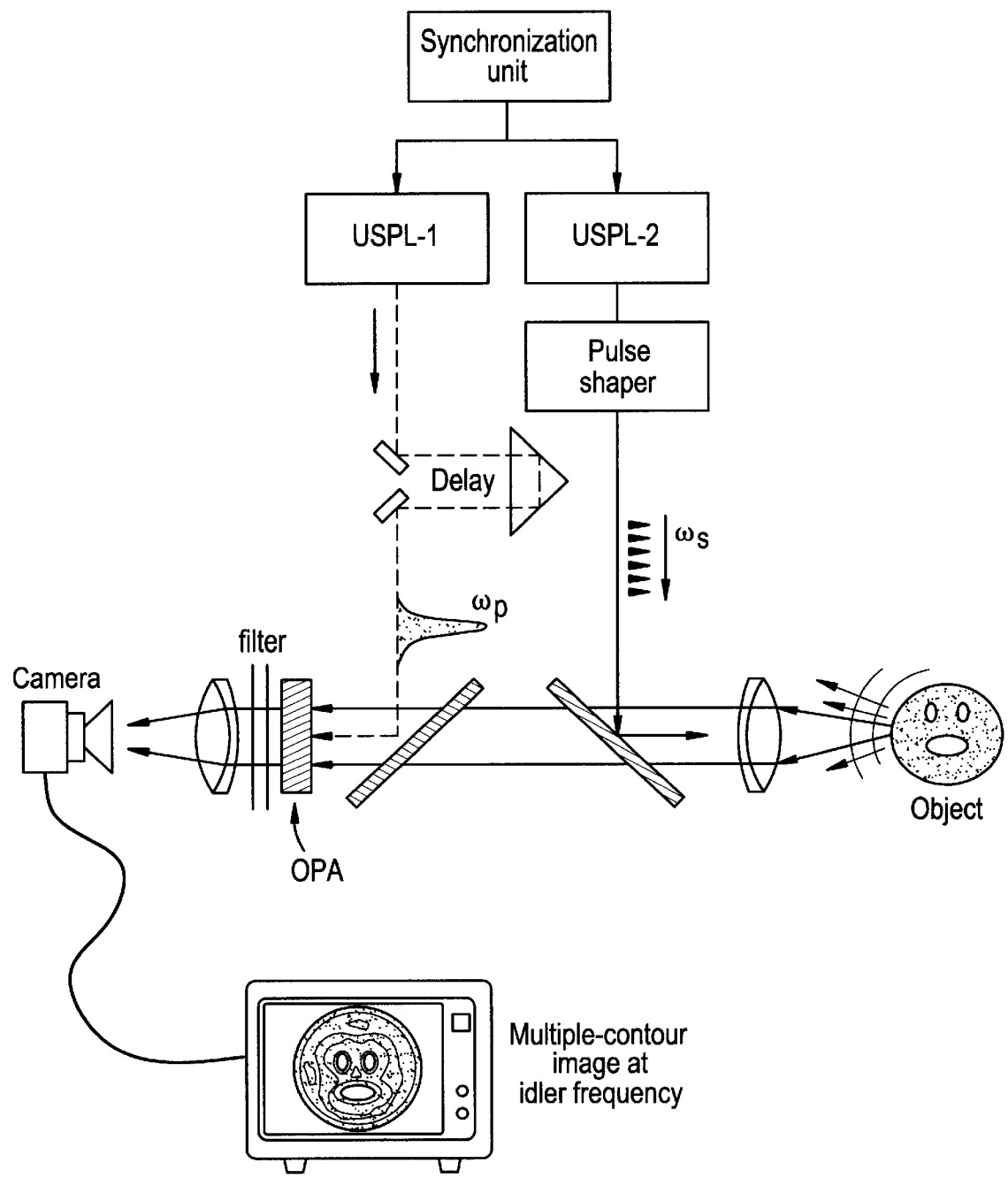
FIG. 7 is a schematic diagram of an imaging system according to another embodiment of the present invention in which the pump pulse and the signal pulse originate from separate laser systems which are synchronized by an electronic synchronization circuit.

FIG. 7 illustrates an imaging system 70 in accordance with another embodiment of the present invention, wherein two separate ultrashort pulse laser sources 72 and 74 are used to generate the pump pulses and the signal pulses, respectively. Laser sources 72 and 74 are electronically synchronized via a synchronization unit 76. Using this arrangement, it is no longer necessary to insure that the optical path lengths traveled by the pump pulse and signal pulse are substantially equal to insure coincidence inside the nonlinear optical medium. Near coincidence can be insured by electronically adjusting the timing delay between the two laser sources via synchronization unit 76. (See, U.S. Pat. No. 5,778,016 to Sucha et al.) This synchronization enables topographic sections of surfaces to be obtained by the previously described UTOPIA techniques even for remote objects (e.g., at a range of 100 meters) for which the equivalent optical delay would be impractically large.

In accordance with another embodiment, the optical parametric image amplification technique of the present invention can be applied to confocal microscopy, e.g., imaging in a confocal single-photon excitation, laser fluorescence, microscope system. The intensity point spread function for such a system produces a quadratic dependence in the detected intensity, resulting in the optical sectioning capability of the system, as reported by M. Gu et al. in "Three-dimensional image formation in confocal microscopy under ultra-short-laser-pulse illumination," Journal of Modern Optics, Vol. 42, No. 4, pp. 747–762 (1995).

Figure 8A:
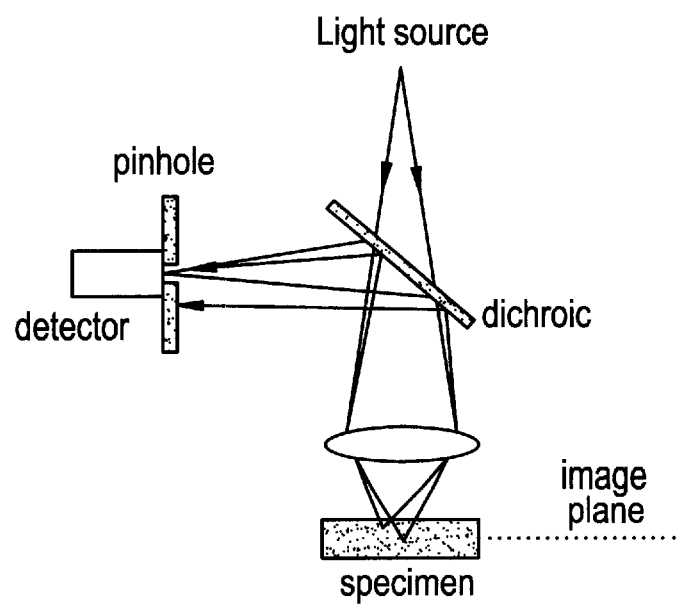
FIG. 8(a) illustrates the basic arrangement of a conventional confocal system.

An example of a single-photon fluorescence microscope 80 having a conventional confocal geometry for imaging in the back-scattered or reflective direction is illustrated in FIG. 8(*a*). Light having a first wavelength is transmitted from light source 82 through dichroic mirror 84 and imaging lens 86 into the specimen 88 along an image plane. The incident light excites a fluorescent medium which has been introduced into the specimen 88, and causes the fluorescent medium to emit light of a different wavelength. The back-scattered light emitted by the fluorescent medium in the specimen 88 is reflected by the dichroic mirror 84 towards a detector 90. The same technique can be applied in a transmissive geometry as well. For the single photon case, in a normal confocal geometry, there will be appreciable fluorescence throughout the focal volume. Hence, a pinhole 92 at the conjugate image plane must be used to block the out-of-focal-plane fluorescence, in order to generate an image.

Because of the intensity-squared dependence, a confocal system is able to produce two-dimensional, cross sectional images of microscopic objects. A series of these two dimensional cross-sections taken at different axial levels within the specimen can be recombined to produce a full high-resolution, three-dimensional image of the specimen. The resolution of this system in part is determined by the pinhole detector size. An infinitely small pinhole produces the highest resolution, but because no photons are detected, the signal-to-noise ratio is zero. Thus, the pinhole size is chosen to yield the most optimal compromise between resolution, and signal-to-noise ratio.

The resolution of a confocal microscopy system can be enhanced by the time gating feature of optical parametric amplification. In accordance with one novel aspect of the present invention, parametric image amplification is used for the first time with confocal imaging systems. The parametric image amplification is to be contrasted with previous parametric image amplification schemes, such as in aforementioned U.S. Pat. No. 3,629,602 to Firester, in that these conventional systems to date have tried, with limited success, to amplify images with high (nonzero) spatial frequency content. By scanning the object with a confocal system, the DC or zero spatial frequency is amplified at all times. The higher spatial frequencies are purposely discriminated against by the confocal system. Thus, while traditional parametric imaging systems are required to account for the effect of the amplification process on the spatial frequency spectral amplitude and phase content of the image, the technique of the present invention need consider only the effect on the amplitude of the DC component. (Spatial frequencies are assigned to the object and the confocal imaging system. The confocal system has a nonzero spatial frequency optical transfer function. This transfer function enables both the illumination beam and the detected fluorescence to be focused to a point. The spatial frequencies described herein refer to those found in the object, not the microscope.) In this manner, amplified images of higher resolution are attainable. Further, by performing confocal parametric image amplification, amplified, high-resolution, three dimensional images are possible for the first time.

In relation to confocal microscopy, the time-gating aspect of the present invention has advantages related to reducing the effects of scattered light. Many multi-photon confocal systems benefit from not having a pinhole at the detector, e.g., the fluorescence or reflected signal does not need to be descanned and the detector can be a two dimensional array such as a CCD, which results in a considerable simplification of the system. In addition, the frame rate capability of this type of confocal system tends to be quite high, readily achieving real-time, video rates for example. The difficulty of many of these systems is that they are unable to discriminate against the scattered light. In accordance with the present invention, parametric image amplification of the signal in these systems is used to time gate against the scattered light, improving the signal-to-background ratio in these systems. Such time gating can also be employed to aid in confocal systems which have pinhole detection.

Referring to FIG. 8(*b*), a confocal microscope 100 in accordance with the present invention includes a nonlinear optical medium 102 placed at the detector location to parametrically amplify the detected signal. No pinhole is provided in this system. An illumination pulse having a signal frequency $\omega_s$ is transmitted through dichroic mirror 104 and imaging lens 106 into a specimen 108 along an image plane. The incident light pulse excites a fluorescent medium which has been introduced into the specimen 108, and causes the fluorescent medium to emit light of a different wavelength. The back-scattered light emitted by the fluorescent medium in the specimen 108 is reflected by the dichroic mirror 104 towards a detector 110. A pump pulse having a pump frequency $\omega_s$ is transmitted from a laser source 112 through dichroic mirror 104 and is incident on nonlinear optical medium 102, such that the pump pulse is spatially and temporally overlapping with the back-scattered light emitted by the fluorescent medium in the specimen 108. The same technique can be applied in a transmissive geometry as well. For purposes of illustration, the pump rays and reflected imaging light rays converging toward the nonlinear optical medium 102 in FIG. 8(*b*) are separated spatially; specifically, the imaging light is shown converging at a greater angle than the pump light. It will be understood that, in the actual system, the pump light and reflected imaging light are made to overlap, i.e., they converge at substantially the same angle.

Note that due to the confocality condition, the nonlinear optical medium 102 is not required to be pumped with a planar beam, but can use a focused beam. This is in contrast to traditional parametric image amplification techniques which require an essentially planar pump beam to preserve image fidelity. The amplified signal produced in this manner, results in improvements in signal-to-noise ratio and resolution. Additionally, it can be used to lower the excitation power of the illuminating beam, which results in increased observation time (bleaching rates are lowered) and enhanced cell viability. In general, cells absorb the short wavelength excitation light, resulting in aberrant behavior or cell death. By lowering the excitation powers necessary for imaging, the cells absorb less energy, and remain viable for longer periods. These improvements are due to the gain provided by parametric amplification.

Assuming square pulses (in time) these gains can be roughly estimated. Time gating with a 100-fs pulse of the detected fluorescence results in a net reduction of photons by (100-fs gate)/(1–10-ns fluorescence)=$10^4$ to $10^5$ when detected at the background free (idler) frequency. (Clearly, this method also benefits by using a gating pulse of 1 to 10 ns in duration—roughly equivalent to the fluorescent lifetime of the reporter molecule. Alternatively, a "burst" of gating pulses can be used, the burst lasting for the fluorescent lifetime. The number of pulses in the burst can be as many as can be conveniently produced.) However, assuming a conservative gain of $10^6$ amplification, there still is a net gain of 10–100. This conservative gain number is used, since the parametric amplification process also creates noise photons. At these gains, the parametric noise is minimal and there is a net increase in overall image signal-to-noise ratio. Thus, the pinhole can be reduced in size proportionately without sacrificing signal-to-noise ratio. By detecting at the signal frequency there is no reduction of the net photons, simply the net gain of $10^6$ in signal over the gating pulse period. Note that, in this simple example, the fact that an incoherent source is being amplified has been ignored. Only the dipoles aligned with the correct polarization to be phase-matched in the parametric amplifier will be amplified.

The optical parametric image amplification technique of the present invention can also be applied in a two-photon excitation confocal microscopy system. In two-photon confocal microscopy, a pinhole is not necessary at the detection plane, as the optical sectioning is inherent to the two-photon absorption process that scales as the square of the excitation intensity. See, M. Gu et al., "Effects of a finite-sized pinhole on 3D image formation in confocal two-photon fluorescence microscopy," Journal of Modern Optics, Vol. 40, No. 10, pp. 2009–2024 (1993). However, the combination of two-photon absorption with a pinhole detector does result in a sharper point spread function in the paraxial diffraction theory limit when compared to the single photon case. Thus, parametric image amplification can be employed as in the single photon excitation case, in identical geometries, with comparable or potentially superior gains in resolution.

The optical parametric image amplification technique of the present invention is also applicable when scanning confocal microscopy using pulsed illumination is employed. See, S. Hell et al., "Pulsed and cw confocal microscopy; a comparison of resolution and contrast," Optics Communications, Vol. 113, pp. 144–152 (1994). In this instance, the detected frequency is the excitation frequency as in a standard microscope. The parametric amplified signal in this case is then just the excitation light that is reflected (or transmitted depending on the geometry of the microscope) back from the specimen.

The optical parametric image amplification technique of the present invention is also applicable when harmonic confocal microscopy is used. In this case, a harmonic of the excitation frequency is detected and used for image formation. The harmonic can be generated from the specimen itself, as in third harmonic interface imaging, as reported by M. Muller et al. in "3D-microscopy of transparent objects using third-harmonic generation," Journal of Microscopy, Vol. 191, No. 3, pages 256–274, 1998, or can be the result of reporter molecules designed to produce a harmonic of the excitation frequency.

In each of the aforementioned techniques, the optical parametric amplification process has been described as a method of improving the resolution of confocal microscopy instruments. It is important to note, however, that the same embodiment can also be used simply to amplify a weak image. The parametric amplification technique can then be used as previously described, but no additional reduction in pinhole size is necessary. This results in an increase in image intensity, but no increase in image resolution. Conversely, the excitation power can be lowered to reduce damage to the specimen, and the parametric amplification used to compensate for the lower power. In this manner, the image remains comparable in resolution and signal-to-noise ratio, but the specimen is exposed to less damaging radiation, thus extending specimen viability.

The application of time gating with optical parametric amplification to discriminate against scattered signals can achieve the same effect as optical coherence tomography (OCT). To date, most OCT systems for imaging through scattering media accomplish this discrimination through interferometry, though recently attempts have been made at imaging in diffuse media using degenerate optical parametric amplification, as reported in the aforementioned article by J. Watson et al. Improvements in the sectioning discrimination and the penetration depth have been obtained by combining OCT with confocal microscopy, as described by Izatt et al. in "Optical coherence microscopy in scattering media," Optics Letters, Vol. 19, p. 590 (1994). The advantage of time gating in the non-degenerate case is that interferometric sensitivity is not required, and background free operation is possible. In the case of degenerate OPA, the system is essentially a form of OCT, but provides amplification without any additional background noise from a "local oscillator," as occurs with the heterodyne gain obtained with conventional OCT systems. Further, phase information from the illuminating beam may be more readily extracted in the time gating geometry as opposed to the interferometric, using for example, any of a number of the recently developed frequency-resolved optical gating schemes. See, e.g., R. Trebino et al., "Measuring ultrashort laser pulses in the time-frequency domain using frequency-resolved optical gating," Rev. Sci. Instrum. 68 (9), September 1997.

By operating the confocal UTOPIA system in the degenerate mode (i.e., $\omega_s=\omega_1$), the gain becomes interferometrically sensitive to the relative optical phase between the pump pulse and the signal pulse scattered from the object. In this case, the system is a particular form of OCT in which the signal gain is provided by parametric amplification rather than by the heterodyne gain mechanism present in conventional OCT. This circumvents certain disadvantages of heterodyne gain, the chief one being the increase in noise background induced by the strong "local oscillator." Since parametric amplification is inherently quiet, this system provides the advantages of OCT systems with a quieter mechanism for signal amplification. This system can be implemented using the configuration shown in FIG. 8(b). The time delay between the pump and signal pulses is rapidly scanned, as in an OCT system.

Figure 8B:
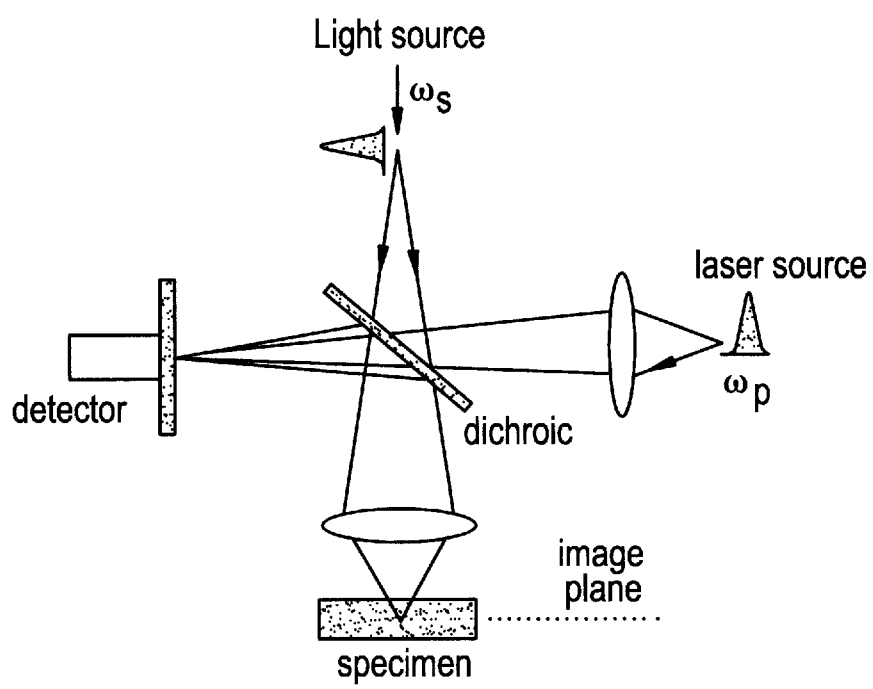
FIG. 8(b) illustrates a confocal system which employs optical parametric amplification in accordance with the present invention.
Figure 9:
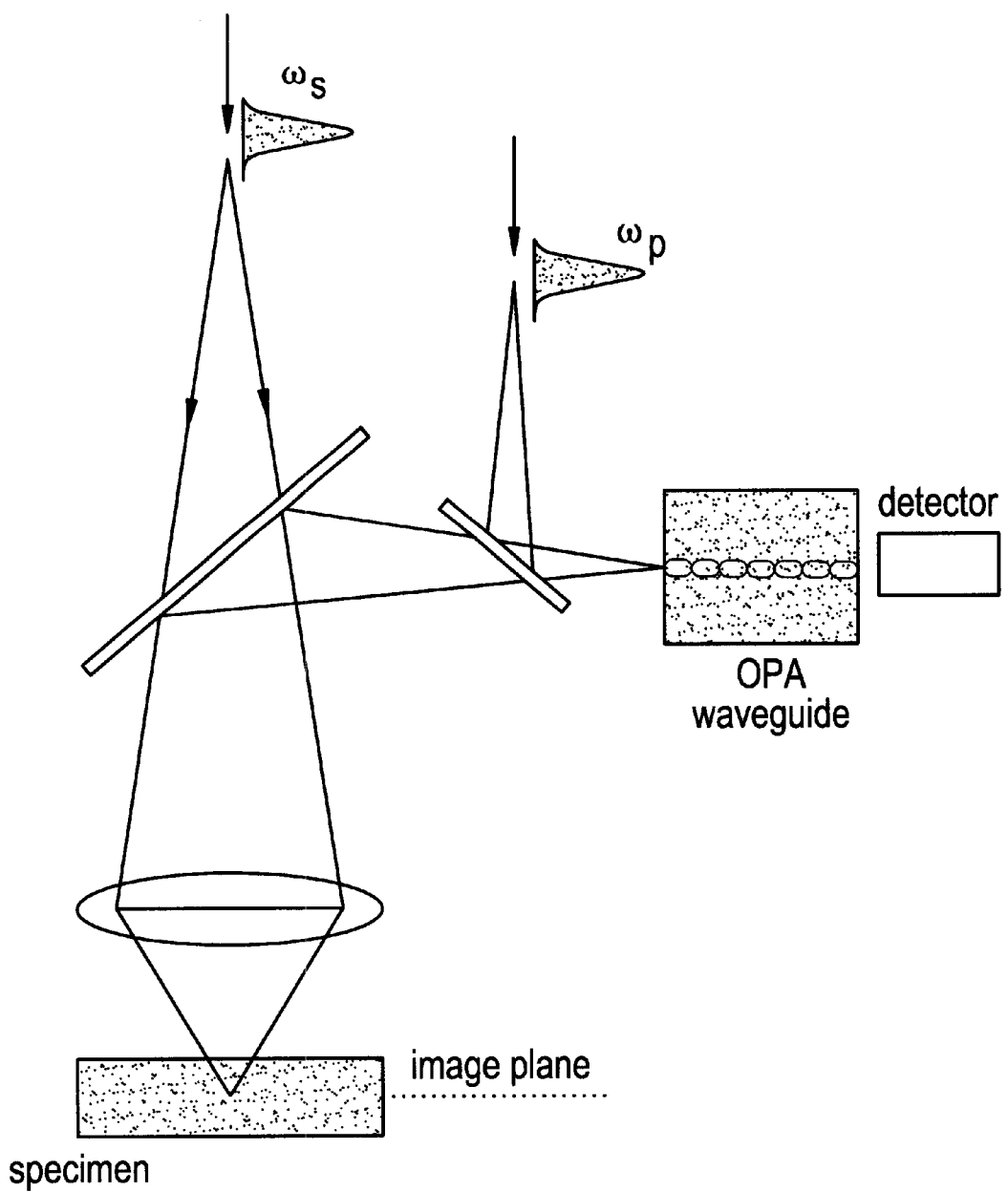
FIG. 9 is a schematic diagram of a parametrically amplified confocal imaging system using a waveguide nonlinear optical medium as the amplifying medium and as the limiting aperture.

The system shown in FIG. 8(b) is essentially a bulk optic system. Referring to FIG. 9, an imaging system 120 in accordance with another embodiment of the present invention includes a nonlinear optical medium formed in a PPLN (or other QPM) waveguide structure 122. In this case, no additional aperture (e.g., a pinhole or the like) is required near the detector because the single-mode nature of the waveguide provides an effectively very small aperture. The advantage of the nonlinear optical medium waveguide structure 122 is that it has a greatly reduced pump power requirement, allowing the use of a simple modelocked laser oscillator (unamplified) as the pump source. This feature provides a great reduction in system size, complexity and cost.

In accordance with another embodiment of the present invention, the combination of optical parametric amplification and confocal microscopy can be used to make fluorescent lifetime imaging measurements. In this case, the actual geometry of the imaging system remains the same as in FIG. 8(b). However, two gating pulses are used which are separated by a variable time delay. Two separate images are formed: one with the first gating pulse, and one with the second gating pulse. The first image is then divided by the second. The value of this ratio is related to the local lifetime of the reporter molecule. For instance, if there has been little lifetime decay the ratio is approximately unity. For substantial decay, the ratio approaches zero. A previously determined look-up-table (LUT) assigns a value to the fluorescent lifetime on a pixel-to-pixel basis within the image. A series of these images taken with various time delays between the two gating pulses increases the accuracy of the technique.

This method has the advantage over other lifetime imaging techniques in that very slow detectors can be used, and saturation of the molecule (which results in a loss of image resolution) is not required as in double pulse fluorescent lifetime imaging. See, A. Buist et al. "Double pulse fluorescent lifetime measurements," Journal of Microscopy, 186 (3) 212 (1997). Further, this technique works with either single photon or two photon excitation, in contrast to those techniques that require saturation of the fluorophore.

Having described preferred embodiments of a new and improved method and apparatus for optical sectioning and imaging using time-gated parametric image amplification, it is believed that other modifications, variations and changes will be suggested to those skilled in the art in view of the teachings set forth herein. It is therefore to be understood that all such variations, modifications and changes are believed to fall within the scope of the present invention as defined by the appended claims.

The disclosures of all of the aforementioned articles and patents are incorporated herein by reference in their entireties.

What is claimed is:

1. An ultrafast time-gated optical parametric amplification system using time-gated optical parametric amplification of light received from an object, comprising:
    an ultrashort pulse laser system configured to generate an optical illumination beam at an illumination frequency and an ultrashort optical pump pulse at a pump frequency, said ultrashort pulse laser system directing the optical illumination beam toward the object;
    a nonlinear optical medium arranged to receive reflected light from the object at a signal frequency in response to interaction of the optical illumination beam with the object, said ultrashort pulse laser system pumping said nonlinear optical medium with the pump pulse, such that the pump pulse spatially and temporally overlaps a portion of the light from the object within the nonlinear optical medium, resulting in time-gating and optical parametric amplification of the portion of the light from the object from interaction with the pump pulse within said nonlinear optical medium; and
    an optical detector responsive to output light emitted by the nonlinear optical medium to produce detection signals.

2. The system according to claim 1, wherein said optical parametric amplification system operates as a LIDAR.

3. The system according to claim 1, wherein said optical parametric amplification system images an object, and said system further comprises an imaging device adapted to form an image of the object in accordance with said detection signals, said detection signals comprising object image signals.

4. The system according to claim 1 or 3, wherein said object is a three dimensional object and said ultrashort pulse laser system comprises a synchronizer for controlling a relative timing of the optical illumination beam and the pump pulse in order to control which portion of the light from the object is parametrically amplified and time-gated by the pump pulse within said nonlinear optical medium, thereby rendering an image of a desired two dimensional section of the three dimensional object.

5. The system according to claim 4, wherein said synchronizer includes a variable optical delay device adapted to adjust the length of an optical path of the pump pulse to control a relative timing of the arrival of the pump pulse and the arrival of the light from the object at said nonlinear optical medium.

6. The system according to claim 1 or 3, wherein said ultrashort pulse laser system comprises:
    an ultrashort pulse laser configured to generate the optical illumination beam and the pump pulse from a common pulse;
    a frequency converter adapted to convert a frequency of the optical illumination beam to the illumination frequency; and
    a variable optical delay device adapted to adjust the length of an optical path of the pump pulse to control a relative timing of the arrival of the pump pulse and the arrival of the light from the object at said nonlinear optical medium.

7. The system according to claim 6, wherein:
    said ultrashort pulse laser comprises a laser source adapted to generate a primary ultrashort optical pulse at a first frequency; and
    said frequency converter comprises: a frequency doubler responsive to the primary ultrashort optical pulse to generate the pump pulse; and an optical parametric generator responsive to the pump pulse to generate the optical illumination beam.

8. The system according to claim 6, wherein said frequency converter comprises at least one of: a second harmonic generator; an optical parametric generator; and a frequency mixer.

9. The system according to claim 6, wherein said variable optical delay device comprises an adjustable optical delay line.

10. The system according to claim 1 or 3, wherein said ultrashort pulse laser system comprises:
    a first ultrashort pulse laser adapted to generate the optical illumination beam;
    a second ultrashort pulse laser adapted to generate the pump pulse;

a synchronizer coupled to the first and second ultrashort pulse lasers, for controlling a relative timing of the arrival of the pump pulse and the arrival of the light from the object at said nonlinear optical medium; and a frequency converter adapted to convert a frequency of the optical illumination beam to the illumination frequency.

11. The system according to claim 10, wherein said synchronizer is an electronic synchronization unit.

12. The system according to claim 1 or 3, wherein the output light detected by said optical detector includes amplified light at the signal frequency generated from the interaction of the light from the object with the pump pulse within said nonlinear optical medium.

13. The system according to claim 1 or 3, wherein the output light detected by said optical detector includes light at an idler frequency generated from the interaction of the light from the object with the pump pulse within said nonlinear optical medium.

14. The system according to claim 13, wherein said pump pulse causes nondegenerate optical parametric amplification of the light from the object within said nonlinear optical medium, such that a frequency-converted signal is generated at the idler frequency which is different from the signal frequency, the system further comprising:

an optical filter disposed in an optical path between said nonlinear optical medium and said optical detector, said optical filter blocking light emitted from the nonlinear optical medium at the signal frequency.

15. The system according to claim 13, wherein:

said pump pulse causes degenerate optical parametric amplification of the light from the object within said nonlinear optical medium, such that the idler frequency is the same as the signal frequency: and the output light includes amplified light at the signal frequency generated from the interaction of the light from the object with the pump pulse within the nonlinear optical medium and unamplified light at the signal frequency.

16. The system according to claim 1 or 3, further comprising:

an optical filter disposed in an optical path between said nonlinear optical medium and said optical detector, said optical filter blocking light emitted from the nonlinear optical medium at the pump frequency.

17. The system according to claim 1 or 3, wherein said nonlinear optical medium is disposed at a real image plane within the system.

18. The system according to claim 1 or 3, wherein said nonlinear optical medium is disposed at a Fourier plane within the system.

19. The system according to claim 1 or 3, wherein said nonlinear optical medium is disposed at a plane other than a real image plane and a Fourier plane within the system.

20. The system according to claim 1 or 3, wherein said nonlinear optical medium is a quasi-phase-matched nonlinear optical crystal.

21. The system according to claim 20, wherein the quasi-phase-matched nonlinear optical crystal is a periodically-poled lithium niobate crystal.

22. The system according to claim 1 or 3, wherein said nonlinear optical medium is an optical waveguide structure.

23. The system according to claim 1 or 3, wherein said nonlinear optical medium is a periodically poled ferroelectric optical material comprising one of a lithium niobate crystal, a lithium tantalate crystal, an MgO:LiNbO$_3$ crystal, and a KTP or KTP isomorph family crystal.

24. The system according to claim 3, wherein said imaging device forms a surface contour image of the object.

25. The system according to claim 3, wherein said object is a three dimensional object and said imaging device forms a two dimensional cross-sectional image of the three dimensional object.

26. The system according to claim 1 or 3, wherein said ultrashort pulse laser system generates the optical illumination beam as a single ultrashort optical pulse at the illumination frequency.

27. The system according to claim 1 or 3, wherein:

said ultrashort pulse laser system comprises a pulse shaper adapted to produce an optical illumination beam that comprises a sequence of ultrashort optical pulses;

a plurality of pulses in the sequence of pulses interacts with a single pump pulse within said nonlinear optical medium, such that said single pump pulse time gates and parametrically amplifies each of the plurality of pulses; and said optical detector detects output light corresponding to each of said plurality of pulses.

28. The system according to claim 27, wherein said pulse shaper controls temporal spacings and relative pulse intensities of pulses in the sequence of ultrashort optical pulses.

29. The system according to claim 1 or 3, wherein said ultrashort pulse laser system generates laser pulses having a pulsewidth of less then 2 ns.

30. The system according to claim 3, wherein:

said ultrashort pulse laser system comprises a pulse shaper adapted to produce an optical illumination beam comprises a sequence of ultrashort optical pulses;

a plurality of pulses in the sequence of pulses interacts with a single pump pulse within said nonlinear optical medium, such that said single pump pulse time gates and parametrically amplifies each of the plurality of pulses;

said optical detector detects output light corresponding to each of said plurality of pulses; and said imaging device forms a three-dimensional image of a surface of the object or a three-dimensional image of a section of the object from the image detection signals corresponding to said single pump pulse.

31. The system according to claim 3, wherein:

said ultrashort pulse laser system generates a plurality of optical illumination beams and a plurality of corresponding ultrafast optical pulses that are directed toward the object;

said nonlinear optical medium receives light from the object in response to interaction of each of the optical illumination beams with the object; and said ultrashort pulse laser system pumps said nonlinear optical medium with said pump pulses in synchronization with the arrival of light from respective optical illumination beams, such that the relative timing of corresponding optical illumination beams and pump pulses is varied so that a portion of the light from the object amplified for different optical illumination beams corresponds to different portions of the object.

32. The system according to claim 31, wherein said imaging device forms a three-dimensional image of a surface of the object or a three-dimensional image of a section of the object from a plurality of light signals emitted from the nonlinear optical medium corresponding to the plurality of optical illumination beams.

33. The system according to claim 1 or 3, wherein said ultrashort pulse laser system illuminates the object with the optical illumination beam collinearly with an optical axis of said optical detector.

34. The system according to claim 3, wherein the light from the object is light from the illumination beam scattered from a surface of the object, the illumination frequency is the signal frequency, and said imaging device generates a topographic image of the object.

35. The system according to claim 1 or 3, wherein the signal frequency is a third harmonic of the illumination frequency, generated at a surface of the object.

36. The system according to claim 3, wherein the system is a confocal imaging system.

37. The system according to claim 3, wherein:
the output light detected by said optical detector includes light at an idler frequency generated from the interaction of the light from the object with the pump pulse within said nonlinear optical medium;
said pump pulse causes degenerate optical parametric amplification of the light from the object within said nonlinear optical medium, such that the idler frequency is the same as the signal frequency;
the output light includes amplified light at the signal frequency generated from the interaction of the light from the object with the pump pulse within the nonlinear optical medium and unamplified light at the signal frequency; and
the imaging device is operated in a degenerate mode, giving interferometrically sensitive gain.

38. The system according to claim 37, wherein the system is an optical coherence tomography system.

39. The system according to claim 37, wherein a time delay between the pump pulse and the optical illumination beam is adjusted for successive pump pulses in a sequence of pump pulses to effect scanning of the object.

40. An ultrafast time-gated optical parametric amplification system using time-gated optical parametric amplification of light received from an object, comprising:
an ultrashort pulse laser system configured to generate an optical illumination beam at an illumination frequency and an ultrashort optical pump pulse at a pump frequency, said ultrashort pulse laser system directing the optical illumination beam toward the object;
a nonlinear optical medium arranged to receive light from the object at a signal frequency in response to interaction of the optical illumination beam with the object, said ultrashort pulse laser system pumping said nonlinear optical medium with the pump pulse, such that the pump pulse spatially and temporally overlaps a portion of the light from the object within the nonlinear optical medium, resulting in time-gating and optical parametric amplification of the portion of the light from the object from interaction with the pump pulse within said nonlinear optical medium;
an optical detector responsive to output light emitted by said nonlinear optical medium to produce detection signals, wherein
said optical parametric amplification system images an object, and said system further comprises an imaging device adapted to form an image of the object in accordance with said detection signals, said detection signals comprising object image signals, and
said imaging device uses the image detection signals generated by said optical detector to make fluorescence lifetime imaging measurements.

41. An ultrafast time-gates optical parametric amplification system using time-gated optical parametric amplification of light received from an object, comprising:
an ultrashort pulse laser system configured to generate an optical illumination beam at an illumination frequency and an ultrashort optical pump pulse at a pump frequency, said ultrashort pulse laser system directing the optical illumination beam toward the object;
a nonlinear optical medium arranged to receive light reflected from the object at a signal frequency in response to interaction of the optical illumination beam with the object, said ultrashort pulse laser system pumping said nonlinear optical medium with the pump pulse, such that the pump pulse spatially and temporally overlaps a portion of the light from the object within the nonlinear optical medium, resulting in time-gating and optical parametric amplification of the portion of the light from the object from interaction with the pump pulse within said nonlinear optical medium; and
an optical detector responsive to output light emitted by said nonlinear optical medium to produce detection signals.

42. A method of imaging an object using time-gated optical parametric amplification of light received from the object, the method comprising the steps of:
transmitting an optical illumination beam, at an illumination frequency, toward the object;
receiving imaging light, at a signal frequency, from the object in response to interaction of the illumination beam with the object, and directing the imaging light into a nonlinear optical medium;
pumping the nonlinear optical medium with an ultrashort optical pump pulse, at a pump frequency, that spatially and temporally overlaps a portion of the imaging light within the nonlinear optical medium, resulting in time-gating and optical parametric amplification of the portion of the imaging light from interaction with the pump pulse within the nonlinear optical medium; and
forming an image of the object in response to output light emitted from the nonlinear optical medium.

43. The method according to claim 42, wherein the output light used to form the image of the object includes amplified light at the signal frequency generated from the interaction of the imaging light with the pump pulse within the nonlinear optical medium.

44. The method according to claim 42, wherein the output light used to form the image of the object includes light at an idler frequency generated from the interaction of the imaging light with the pump pulse within the nonlinear optical medium.

45. The method according to claim 44, wherein nondegenerate optical parametric amplification of the imaging light results from interaction of the imaging light with the pump pulse, such that a frequency-converted image signal is generated at the idler frequency which is different from the signal frequency, the method further comprising the step of:
filtering out light emitted from the nonlinear optical medium at the signal frequency, such that the output light used to form the image of the object does not include light at the signal frequency.

46. The method according to claim 44, wherein:
degenerate optical parametric amplification of the imaging light results from interaction of the imaging light with the pump pulse, such that the idler frequency is the same as the signal frequency; and
the output light used to form the image of the object includes amplified light at the signal frequency generated from the interaction of the imaging light with the pump pulse within the nonlinear optical medium and unamplified light at the signal frequency.

47. The method according to claim 42, further comprising the step of:
filtering out light emitted from the nonlinear optical medium at the pump frequency, such that the output light used to form the image of the object does not include light at the pump frequency.

48. The method according to claim 42, further comprising the step of positioning the nonlinear optical medium at a real image plane within an imaging system.

49. The method according to claim 42, further comprising the step of positioning the nonlinear optical medium at a Fourier plane within an imaging system.

50. The method according to claim 42, further comprising the step of positioning the nonlinear optical medium at a plane other than a real image plane and a Fourier plane within an imaging system.

51. The method according to claim 42, wherein the pumping step includes pumping the nonlinear optical medium that is a quasi-phase-matched nonlinear optical crystal.

52. The method according to claim 51, wherein the quasi-phase-matched nonlinear optical crystal is a periodically-poled lithium niobate crystal.

53. The method according to claim 42, wherein the pumping step includes pumping the nonlinear optical medium that is a nonlinear optical waveguide structure.

54. The method according to claim 42, wherein said nonlinear optical medium is a periodically poled ferroelectric optical material comprising one of a lithium niobate crystal, a lithium tantalate crystal, an MgO:LiNbO$_3$ crystal, and a KTP or KTP isomorph family crystal.

55. The method according to claim 42, wherein the image formed of the object is a surface contour of the object.

56. The method according to claim 42, wherein the object is a three dimensional object and the image formed of the three dimensional object is a two dimensional cross-section of the object.

57. The method according to claim 42, wherein the optical illumination beam corresponding to a single pump pulse comprises a single ultrashort optical pulse at the illumination frequency.

58. The method according to claim 42, wherein the optical illumination beam comprises a sequence of ultrashort optical pulses that are time gated and parametrically amplified within the nonlinear optical medium by a single pump pulse, and wherein the image of the object comprises a plurality of images of different portions of the object respectively corresponding to the sequence of ultrashort optical pulses.

59. The method according to claim 58, further comprising the step of controlling temporal spacings and relative pulse intensities of pulses in the sequence of ultrashort optical pulses.

60. The method according to claim 58, wherein the plurality of images form a three-dimensional image of a surface of the object or a three-dimensional image of a section of the object.

61. The method according to claim 42, wherein the optical illumination beam and the pump pulse are derived from a common pulse.

62. The method according to claim 42, wherein the optical illumination beam is frequency converted relative to the pump pulse, such that the illumination frequency of the optical illumination beam is less than the pump frequency of the pump pulse.

63. The method according to claim 42, further comprising the steps of:

transmitting a second optical illumination beam toward the object;

receiving second imaging light from the object in response to interaction of the second illumination beam with the object, and directing the second imaging light into the nonlinear optical medium; and pumping the nonlinear optical medium with a second ultrashort optical pump pulse that spatially and temporally overlaps a portion of the second imaging light within the nonlinear optical medium, wherein a timing of the second pump pulse relative to the second imaging light is different from a timing of the pump pulse relative to the imaging light, such that the portion of the second imaging light amplified by the second pump pulse images a different portion of the object than the amplified portion of the imaging light.

64. The method according to claim 42, wherein:
the transmitting step includes transmitting a plurality of optical illumination beams;
the pumping step includes pumping the nonlinear optical medium with a plurality of ultrafast optical pump pulses in synchronization with the plurality of optical illumination beams; and
the relative timing of corresponding illumination beams and pump pulses is varied such that the portion of the imaging light amplified for different optical illumination beams corresponds to different portions of the object.

65. The method according to claim 64, wherein the forming step includes forming a three-dimensional image of the object from a plurality of light signals emitted from the nonlinear optical medium corresponding to the plurality of illumination beams.

66. The method according to claim 42, further comprising the step of controlling a relative timing of the arrival of the pump pulse and the arrival of the imaging light at the nonlinear optical medium to control which portion of the imaging light is parametrically amplified and time-gated by the pump pulse, thereby controlling which portion of the object is imaged.

67. The method according to claim 42, wherein the object is illuminated by the illumination beam collinearly with an optical axis of the nonlinear optical medium.

68. The method according to claim 42, wherein the imaging light is light from the illumination beam scattered from a surface of the object, the illumination frequency is the signal frequency, and the image of the object is a topographic image.

69. The method according to claim 42, wherein the
the object is a three dimensional object,
the illumination beam excites a fluorescent medium introduced into the object, causing the fluorescent medium to emit the imaging light at the signal wavelength which is different from the illumination wavelength, and
the image of the three dimensional object is a two dimensional cross-sectional image.

70. The method according claim 42, wherein the signal frequency is a harmonic of the illumination frequency.

71. The method according to claim 42, wherein the image of the object is used to make fluorescence lifetime imaging measurements.

72. A method of imaging an object using time-gated optical parametric amplification of light received from the object, the method comprising the steps of:

transmitting an optical illumination beam, at an illumination frequency, toward the object;

receiving imaging light, at a signal frequency, from the object in response to interaction of the illumination beam with the object, and directing the imaging light into a nonlinear optical medium;

pumping the nonlinear optical medium with an ultrashort optical pump pulse, at a pump frequency, that spatially and temporally overlaps a portion of the imaging light within the nonlinear optical medium, resulting in time-grating and non-degenerate optical parametric amplification of the portion of the imaging light from interaction with the pump pulse within the nonlinear optical medium; and forming an image of the object in response to output light emitted from the nonlinear optical medium.

73. An ultrafast time-gated optical parametric amplification system using time-gates optical parametric amplification of light received from an object, comprising:

an ultrashort pulse laser system configured to generate an optical illumination beam at an illumination frequency and an ultrashort optical pump pulse at a pump frequency, said ultrashort pulse laser system directing the optical illumination beam toward the object;

a nonlinear optical medium arranged to receive light from the object at a signal frequency in response to interaction of the optical illumination beam with the object, said ultrashort pulse laser system pumping said nonlinear optical medium with the pump pulse, said that the pump pulse spatially and temporally overlaps a portion of the light from the object within the nonlinear optical medium, resulting in time-gating and non-degenerate optical parametric amplification of the portion of the light from the object from interaction with the pump pulse within said nonlinear optical medium; and an optical detector responsive to output light emitted by said nonlinear optical medium to produce detection signals.

74. The system according to claim 73, wherein said optical parametric amplification system images an object, and said system further comprises an imaging device adapted to form an image of the object in accordance with said detection signals, said detection signals comprising object image signals.

75. The system according to claim 73 or 74, wherein:

said ultrashort pulse laser system generates a second optical illumination beam and a second optical pump pulse, said ultrashort pulse laser system directing the second optical illumination beam toward the object; and said nonlinear optical medium receives second light from the object in response to interaction of the second optical illumination beam with the object, said ultrashort pulse laser system pumping said nonlinear optical medium with the second pump pulse, so that the second pump pulse spatially and temporally overlaps a portion of the second imaging light within the nonlinear optical medium, whereby a timing of the second pump pulse relative to the second light from the object is different from a timing of the pump pulse relative to the first light from the object, such that the portion of the second light amplified by the second pump pulse corresponds to a different portion of the object than the amplified portion of the first light from the object.

76. The system according to claim 74, wherein the illumination beam excites a fluorescent medium introduced into the object, causing the fluorescent medium to emit imaging light at the signal wavelength which is different from the illumination wavelength, and said imaging device generates a cross-sectional image of the object.

* * * * *